(12) United States Patent
Iwase et al.

(10) Patent No.: US 6,960,359 B2
(45) Date of Patent: Nov. 1, 2005

(54) INTERLEUKIN-4 PRODUCTION INHIBITORS

(75) Inventors: Norikazu Iwase, Tokyo (JP); Norihiro Tanaka, Tokyo (JP); Hirotaka Sato, Tokyo (JP); Kazuyuki Fukuda, Tokyo (JP); Mami Nonomura, Tochigi (JP); Yoshiaki Ichikawa, Tochigi (JP); Kimihiko Hori, Tochigi (JP)

(73) Assignee: Kao Corporation, Tokyo (JP)

( * ) Notice: Subject to any disclaimer, the term of this patent is extended or adjusted under 35 U.S.C. 154(b) by 7 days.

(21) Appl. No.: 10/279,936

(22) Filed: Oct. 25, 2002

(65) Prior Publication Data

US 2003/0129266 A1 Jul. 10, 2003

Related U.S. Application Data

(62) Division of application No. 09/510,530, filed on Feb. 22, 2000, now abandoned.

(30) Foreign Application Priority Data

Feb. 22, 1999 (JP) ............................................ 11-042725
Oct. 28, 1999 (JP) ............................................ 11-307327

(51) Int. Cl.$^7$ ............................................... A61K 35/78
(52) U.S. Cl. ...................................................... 424/725
(58) Field of Search ......................... 424/725; 514/861, 514/863

(56) References Cited

U.S. PATENT DOCUMENTS

| | | | |
|---|---|---|---|
| 2,863,804 | A | 12/1958 | Fuqua |
| 4,229,466 | A | 10/1980 | Miyazaki et al. |
| 4,318,906 | A | 3/1982 | Llopart |
| 4,874,782 | A | 10/1989 | Bonjouklian et al. |
| 5,057,501 | A | 10/1991 | Thornfeldt |
| 5,141,666 | A | 8/1992 | Yorozu et al. |
| 5,302,522 | A | 4/1994 | Takigawa et al. |
| 5,397,497 | A | 3/1995 | Jakobson et al. |
| 5,571,516 | A | 11/1996 | Tezuka et al. |
| 5,753,270 | A | 5/1998 | Beauchamp et al. |
| 5,849,310 | A | 12/1998 | Trinh et al. |
| 5,958,462 | A | 9/1999 | McLean |
| 5,985,292 | A | 11/1999 | Fourneron et al. |
| 6,132,756 | A | 10/2000 | Haque et al. |
| 6,190,685 | B1 | 2/2001 | Karita |
| 6,495,171 | B2 | 12/2002 | Iwase et al. |

FOREIGN PATENT DOCUMENTS

| | | |
|---|---|---|
| CH | 688 787 | 3/1998 |
| DE | 41 25 871 | 3/1993 |
| DE | 195 40 462 | 5/1997 |
| DE | 299 13 476 | 10/1999 |
| DE | 198 24 681 | 12/1999 |
| EP | 0 308 210 | 3/1989 |
| EP | 0 507 295 | 10/1992 |
| FR | 2504551 | 10/1982 |
| FR | 2 729 856 | 8/1996 |
| FR | 2729859 | 8/1996 |
| FR | 2753092 | 3/1998 |
| GB | 2309902 | 8/1997 |
| JP | 61-027910 | 2/1986 |
| JP | 62-45517 | 2/1987 |
| JP | 1-151522 | 6/1989 |
| JP | 3-109317 | 5/1991 |
| JP | 03-145430 | 6/1991 |
| JP | 4-23967 | 1/1992 |
| JP | 5-306218 | 11/1993 |
| JP | 5-306219 | 11/1993 |
| JP | 5-331047 | 12/1993 |
| JP | 6-16515 | 1/1994 |
| JP | 06-016515 | 1/1994 |
| JP | 6-80557 | 3/1994 |
| JP | 07-61918 | 3/1995 |
| JP | 7-97591 | 4/1995 |
| JP | 7-97600 | 4/1995 |
| JP | 7188046 | 7/1995 |
| JP | 09-077665 | 9/1995 |
| JP | 08-103402 | 4/1996 |
| JP | 8-188529 | 7/1996 |
| JP | 09-031858 | 2/1997 |
| JP | 09-143119 | 6/1997 |
| JP | 10-036246 | 2/1998 |
| JP | 10036247 | 2/1998 |
| JP | 10-87409 | 4/1998 |
| JP | 10036246 | 4/1998 |
| JP | 10-167957 | 6/1998 |
| JP | 10-279491 | 10/1998 |
| JP | 11-199500 | 7/1999 |
| JP | 2000-86529 | 3/2000 |
| JP | 2000-95680 | 4/2000 |
| JP | 2000-309524 | 11/2000 |
| RU | 2107510 | 3/1998 |
| WO | WO 98/01134 | 1/1998 |
| WO | WO 98/17749 | 4/1998 |
| WO | WO 98/32444 | 7/1998 |
| WO | WO 00/16752 | 3/2000 |

OTHER PUBLICATIONS

Elbe–Buerger et al., Journal of Investigative Dermatology, (May 2002), 118(5): 767–778. Overexpression of IL–4 alters the homeostasis in the skin.*

(Continued)

Primary Examiner—Michele Flood
(74) Attorney, Agent, or Firm—Oblon, Spivak, McClelland, Maier & Neustadt, P.C.

(57) ABSTRACT

This invention relates to IL-4 production inhibitors, anti-allergic agents and atopic dermatitis preventives and improvers, each of which contains at one or more compounds selected from the group consisting of hydroxyl-containing monoterpenes, hydroxyl-containing sesquiterpenes and their acylated derivatives. This invention is also concerned with IL-4 production inhibitors, antiallergic agents and atopic dermatitis preventives and improvers, each of which contains an essential oil such as cedarwood oil. This invention is also concerned with bath medicine compositions, each of which contains one or more ingredients selected from cedrol, cedrenol, farnesol, patchouli alcohol and vetiverol.

21 Claims, No Drawings

OTHER PUBLICATIONS

Yi–Chang Lu, "Studies on the Chemical Constituents of HE Essential OIT of Rhododendron Tsinghaiense Ching", Hua Hsueh Hsueh Pao, 1980, vol. 38, No. 3, pp. 241–249 (1 page English Abstract).

Xiull Ma, et al., "Biosynthesis of LTB4 and Selection of its Inhibitors", Baiqiuen Yike Daxue Xuebao, (Database Chem Abstracts), 1990, vol. 16, No. 3, pp. 222–225.

U.R. Juergens, et al., "The Anti–Inflammatory Activity of I–Menthol Compared to Mint Oil in Human Monocytes In Vitro: A Novel Perspective for its Therapeutic Use in Inflammatory Diseases", European Journal of Medical Research, Dec. 16, 1998, vol. 3, pp. 539–545.

A.W. Frankland, Rrhinitis, Allergic, Encyclopedia of Immunology, 1992, pp. 1343–1346.

Th.Werfel, et al., "Zytokine Als Mediatoren Allergischer Organreaktionen", Allergologie, 1997, vol. 20, No. 11, pp. 546–550 (Cytokines as Mediators of Allergic Tissue Response).

M.F. Beylier, "Bacteriostatic Activity of Some Australian Essential Oils", Perfuner & Flavorist, Apr./May 1979, vol. 4, pp. 23–24.

J. Retamar, et al., "Esstial Oil of Matricaria Recutita", Essenze Derivati Agrumari, 1989, No. 1, pp. 40–43.

"Cedarwood Oil", 1998, pp. 39–413 (XP–002152519—1 page Abstract).

Y. Kawasaki, et al., "The Role of Fragrance in Bath Preparations", Perfume, Dec. 1990, No. 168, Nippon Perfume Association, pp. 91–97 and 154.

A. Shoten, "Cedar and Patchouli", Encyclopedia of Fragrance, Nippon Perfume Association, pp. 251–253 and pp. 299–302.

M. Indoh, "Synthesized Perfume", Knowledge of Chemistry and Products, Author of Motokazu Indoh Kagaku Kogyo Nipposha, Mar. 6, 1996.

M. Yoshimura, et al., "Fragrances of Bath Preparations and Their Research Trends", Fragrance Journal, Fragrance Journal Co., Ltd., Nov. 1994, pp. 37–45 and p. 119 (English Abstract).

K. Yoshikawa, "Clinical Evaluation of Children's Skin Care Product Containing Beta–Thujaplicin (Hinokitiol): Study and Usefulness of Bean Stalk Series (BS–1210):Body Shampoo, Oil and Medicated Cream", Skin Research, 1995, 37(1), pp. 136–152.

J. Lawless, The Illustrated Encyclopedia of Essential Oils (1995), Element Books, USA, pp. 36–41, 50–55, 57–58, 62, 108, 156–157, 160, 194–195, 204, 214, and 234.

A.L. Leung, et al., Encyclopedia of Common Natural Ingredients, 1998, pp. 139–141 and 411–413.

Patent Abstracts of Japan, vol. 1998, No. 10, Aug. 31, 1998, JP 10 117657, May 12, 1998.

Chemical Abstracts, vol. 122, No. 20, May 15, 1995 AN 1995:511768, JP 07 033648, Feb. 3, 1995.

Chemical Abstracts, vol. 128, No. 8, Feb. 23, 1998, AN 1998:88110, JP 09 327265, Dec. 22, 1997.

* cited by examiner

INTERLEUKIN-4 PRODUCTION INHIBITORS

This application is a division of application Ser. No. 09/510,530 filed on Feb. 22, 2000, abandoned.

TECHNICAL FIELD

This invention relates to interleukin-4 (hereinafter called "IL-4") production inhibitors, antiallergic agents and atopic dermatitis preventives and improvers, which contain specific monoterpenes, sesquiterpenes or particular essential oils. This invention is also concerned with bath medicine compositions containing specific plant-derived ingredients.

BACKGROUND ART

IL-4 is a substance produced by T lymphocytes which are human or animal immune response cells, and are known to act on B lymphocytes and to enhance production of an antibody such as IgE [Rinsho Meneki (Clinical Immunology), 27, 45–57 (1995)]. For many years IgE is known to take a significant part in the onset of an atopic disease. Further, IL-4 is known to act as an accelerator of inflammatory cell infiltration at lesions in allergic diseases [Cell, 62, 457–467 (1990)]. From these, it is considered that IL-4 is largely implicated in the onset of an allergic disease. Inhibition of IL-4 production, if successfully achieved, is therefore believed to make it possible to treat and prevent allergic diseases more fundamentally from their cause than conventional treatment and preventive methods making use of histamine release inhibitors, IgE or histamine effect inhibitors or the like.

As substances for inhibiting the production of IL-4, a group of sulfonium derivatives including suplatast tosilate is well-known [Japan. J. Pharmacol., 62, 27–30 (1993)]. They are formulated into oral drugs and are used to treat allergic diseases such as atopic dermatitis, itching and pruritus, and the like, but their effects are not sufficient. In addition, their administration routes are limited because they have low percutaneous or transdermal absorption due to their structures. There is hence an outstanding need for IL-4 production inhibitors, antiallergic agents, and atopic dermatitis preventives and improvers, which are excellent in percutaneous or transdermal absorption, stability and safety.

In the case of one having overdrying skin or oversensitive skin and one suffering from atopic dermatitis, on the other hand, the skin is especially sensitive so that the skin tends to develop itching, pruritus, eczema or the like even by mild stimulation. Further, an allergic reaction to a house dust mite antigen, food or the like, psychological stress or the like acts as a deteriorating factor, thereby tending to result in a skin trouble. Use of medicinal bath preparations (JP 2-115117 A), which were added with conventional oil ingredients or humectants, were not able to sufficiently bring about fundamental preventing and improving effects although moistened skin feeling was available temporarily. There is accordingly an outstanding desire for bath medicine compositions, which have high effectiveness for improving skin roughness or dryness and for preventing and improving atopic dermatitis even for those having overdrying or oversensitive skin.

DISCLOSURE OF THE INVENTION

This invention provides use of at least one compound for the production of an IL-4 production inhibitor, an antiallergic agent or an atopic dermatitis preventive and improver, in which the compound is selected from the group consisting of hydroxyl-containing monoterpenes, hydroxyl-containing sesquiterpenes and acylated derivatives thereof, This invention also provides use of at least one essential oil for the production of an IL-4 production inhibitor, an antiallergic agent or an atopic dermatitis preventive and improver, in which the essential oil is selected from the group selected from the group consisting of cedarwood oil, eucalyptus oil, patchouli oil, sandalwood oil, vetiver oil, guaiacwood oil, bay oil, clove oil, chamomile oil, ginger oil, cumin oil, pepper oil, rosemary oil, hinoki oil, hiba oil, pimentoberry resinoid and myrrh resinoid.

This invention further provides use of at least one compound for the production of an IL-4 production inhibitor, an antiallergic agent or an atopic dermatitis preventive and improver, in which the compound is selected from the group consisting of eugenol, hinokitiol, cineole and acetylcedrene.

This invention still further provides a method for the treatment of a disease caused by production of IL-4, an allergic disease or atopic dermatitis, which comprises administering at least one essential oil selected from the group consisting of cedarwood oil, eucalyptus oil, patchouli oil, sandalwood oil, vetiver oil, guaiacwood oil, bay oil, clove oil, chamomile oil, ginger oil, cumin oil, pepper oil, rosemary oil, hinoki oil, hiba oil, pimentoberry resinoid and myrrh resinoid.

This invention still further provides a method for the treatment of a disease caused by production of IL-4, an allergic disease or atopic dermatitis, which comprises administering at least one compound selected from the group consisting of eugenol, hinokitiol, cineole and acetylcedrene.

Moreover, the present inventors have found that addition of one or more specific fragrance ingredients out of the above-described ingredients makes it possible to provide a bath medicine composition having high effectiveness for improving symptoms such as skin roughness, dryness, eczema and the like and also skin characteristics prone to skin troubles even for those having overdrying skin or oversensitive skin or suffering from atopic dermatitis.

This invention therefore also provides a bath medicine composition comprising at least one ingredient selected from cedrol, cedrenol, farnesol, patchouli alcohol or vetiverol.

This invention further provides use of at least one ingredient for the production of a bath medicine composition, in which the ingredient is selected from cedrol, cedrenol, farnesol, patchouli alcohol or vetiverol.

Furthermore, the present invention provides a bathing method, which comprises bathing in bathwater added with a composition which comprises at least one ingredient selected from cedrol, cedrenol, farnesol, patchouli alcohol or vetiverol.

BEST MODES FOR CARRYING OUT THE INVENTION

Essential oils such as cedarwood oil are found in branches, leaves, roots, stalks, barks, fruits, buds, resins and the like of plants, and owing to the inclusion of abundant volatile ingredients and the possession of characteristic fragrances, are used as ingredients for perfumes. On the other hand, hydroxyl-containing monoterpenes, hydroxyl-containing sesquiterpenes, eugenol, hinokitiol and cineole are found as isolated ingredients of essential oils in branches, leaves and the like of plants. Further, as reaction products of isolated ingredients of essential oils, derivatives such as acetylcedrene and cedryl acetate are used as fragrance ingredients. However, their possession of IL-4 production inhibitory action and the like were not known at all.

Preferred examples of hydroxyl-containing monoterpenes can include l-menthol and citronellole. Preferred examples of hydroxyl-containing sesquiterpenes can include globulol, epiglobulol, farnesol, guaiol, patchouli alcohol, cedrol, santalol, vetiverol, widrrol, thujopsenol and cedrenol. As acylated derivatives, acetylated derivatives are preferred with cedryl acetate being more preferred. Of these, globulol, epiglobulol, farnesol, guaiol, patchouli alcohol, cedryl acetate and cedrol are more preferred, with cedrol being particularly preferred.

Hydroxyl-containing monoterpenes, hydroxyl-containing sesquiterpenes, eugenol, hinokitiol and cineole can be isolated by methods known per se in the art from plants known to contain them. Acetylcedrene, on the other hand, can be obtained by acetylating cedrene which is isolated from cedarwood oil or the like. They may also be chemically synthesized ones.

As these ingredients, known plant extracts, distillate fractions or the like with such ingredients contained therein can be used as they are. Described specifically, essential oils in the form of extracts, resinoids, absolutes or the like—which can be obtained by providing trees, herbs, spices and the like as raw materials and subjecting their wood chips, barks, roots, stalks, leaves, fruits, flowers or the like to extraction, steam distillation, pressing or the like in a manner known per se in the art—can be used as they are. More specifically, it is possible to use, without any further processing or treatment, cedarwood oil as cedrol; eucalyptus oil as globulol or epiglobulol; patchouli oil as patchouli alcohol; bay oil, clove oil or pimentoberry resinoid as eugenol; guiac wood oil as guaiol; hinoki oil as hinokitiol; and cardamon oil or the like as cineole. Illustrative of the above-described trees, herbs, spices and the like are cedar, eucalyptus, patchouli, sandalwood, vetiver, bayberry, clove, chamomile, ginger, cumin, pepper, rosemary, peppermint, valerian, honeysucle, thyme, tea, guaiacwood, hiba, hinoki, pimentoberry, and sage. Concerning these source plants, no particular limitation is imposed on their place of origin, weather, harvesting method, handling method, and the like.

In the present invention, preferred examples of essential oil can include cedarwood oil, eucalyptus oil, patchouli oil, pimentoberry resinoid, vetiver oil, sandalwood oil, bay oil, clove oil, chamomile oil, guaiacwood oil, ginger oil, and cumin oil. Of these, cedarwood oil, eucalyptus oil, patchouli oil, pimentoberry resinoid, vetiver oil and sandalwood oil are more preferred. Still more preferred are cedarwood oil, eucalyptus oil and pimentoberry oil, with cedarwood oil and eucalyptus oil being particularly preferred. Such essential oils can be obtained by methods known per se in the art by using as raw materials plants which contain them.

Such hydroxyl-containing monoterpenes, hydroxyl-containing sesquiterpenes, acylated derivatives thereof, eugenol, hinokitiol, cineole and acetylcedrene, which are useful in the present invention, may have chirality.

Essential oils (hereinafter called "IL-4 production inhibiting substances"), such as these hydroxyl-containing monoterpenes, hydroxyl-containing sesquiterpenes, acylated derivatives thereof, eugenol, hinokitiol, cineole, acetylcedrene, eucalyptus oil and cedarwood oil, have excellent IL-4 production inhibitory activity and are useful for the production of antiallergic agents, especially preventives and improvers for atopic dermatitis, allergic rhinitis and bronchial asthma.

IL-4 is also considered to have some connection to various non-allergic diseases of skin. IL-4 has an effect that it acts on keratinocytes to enhance production of IL-6 [Ann. N.Y. Acad. Sci., 557, 454–465, (1989)], and has been considered to take part in skin inflammation. Further, mast cells stimulated by IL-4 are known to react to endothelin, thereby undergoing a histamine release [J. Immunol., 154, 1830–1837 (1995)]. In view of the fact that endothelin is produced from keratinocytes upon exposure to ultraviolet rays, ultraviolet rays are certainly considered to take part in itching. IL-4 is also known to act on fibroblasts to modify their collagen synthesizing ability [J. Clin. Invest., 90, 1479–1485 (1992)], so that there is possibility that IL-4 may also take part in the development of wrinkles and flabbiness on skin. The IL-4 production inhibitor according to the present invention is therefore expected to be effective for the prevention and treatment of other IL-4-related diseases, namely, itching or pruritus, wrinkles, freckles, dermatophytosis, stomatitis and the like.

The IL-4 production inhibitor, antiallergic agent and atopic dermatitis preventive and improver according to the present invention can be administered as external skin care preparations, oral preparations, injections, inhalants, medicinal bath preparations or the like.

Illustrative of external skin care preparations are ointments, toilet waters, creams, lotions, packs, and foundations. They can be produced by formulating the above-described IL-4 production inhibiting substance, an external skin care base commonly employed in external skin care preparations, one or more other medicinally-effective ingredients and the like in a manner known per se in the art. The external skin care base can be an oil base, an emulsified base of the oil/water or water/oil type, or water. Examples of the oil base can include oils and fats such as vegetable oils and animal oils, higher alcohols, fatty acids, and esters. As illustrative examples of medicinally-effective ingredients, anti-inflammatory analgesics, disinfectants, vitamins, emollients and the like can be used as needed. Further, humectants, ultraviolet absorbers, chelating agents, pH regulators, antiseptics, thickeners, alcohols, colors, perfumes and the like can also be added.

Oral preparations can be obtained by mixing the above-described IL-4 production inhibiting substance with a carrier such as lactose or starch and then forming the resulting mixture into tablets, capsules, granules or powder as needed or by dissolving or dispersing the above-described IL-4 production inhibitor in purified water or the like to provide a liquid preparation, syrup or drink. On the other hand, injections and inhalants can also be prepared by methods known per se in the art.

No particular limitation is imposed on the dose of the above-described IL-4 production inhibitor insofar as it falls within a range commonly adopted for cosmetics, drugs, or quasi-drugs, but a daily dose of from 0.001 to 2000 mg per adult is generally preferred.

For use in the bath medicine composition according to the present invention, one or more ingredients can be selected from cedrol, cedrenol, farnesol, patchouli alcohol and vetiverol. The proportion of such ingredient or ingredients in the bath medicine composition may be 10 ppm or higher, more specifically 0.01 to 20 wt. %, more preferably 1 to 10 wt. % based on all the ingredients. It is preferable to set the one dose of the bath medicine composition such that the concentration of such ingredient or ingredients becomes 0.01 ppm or higher, more specifically 0.1 to 1,000 ppm, more preferably 5.0 to 1,000 ppm in bath water.

In the bath medicine composition according to the present invention, an extract, steam distillate, pressed liquid or the like of a plant containing such an ingredient may also be used.

Examples of such a plant can include cedar, patchouli, and vetiver.

These plants can be subjected to extraction, steam distillation, pressing or the like in a manner known per se in the art. The resulting fraction may be used after fractionating it further or may be used in the form of a further-purified essential oil.

It is particularly preferred to incorporate, in addition to the above-described ingredients, an epidermal lipid or its analogue in the bath medicine composition according to the present invention, because the skin roughness or dryness improving effect can be enhanced further.

Examples of the epidermal lipids and its analogue for use in the present invention can include intercellular corneum lipids such as natural ceramides, ceramide analogues, steroids, fatty acid esters of steroids, fatty acids, and triglycerides; and cerebrosides and phospholipids. Among these, natural ceramides, ceramide analogues, phospholipids and fatty acid esters of steroids are preferred.

As a natural ceramide, it is preferred to use one or more of known type I to type VII which are contained in human epidermal lipids [Hifu Rinsho (Dermatoclinical Medicine), 35, 1147–1161 (1993); Angew. Chem. Int. Ed., 38, 1532–1568 (1999)]. Examples of ceramide analogues can include those represented by the following formulas (1)–(4) and disclosed in JP 63-216812 A [formula (1)], JP 8-319263 A [formula (2)], JP 3-193754 A [formula (3)], JP 4-282304 A [formula (4)] and the like. All of these publications are incorporated herein by reference.

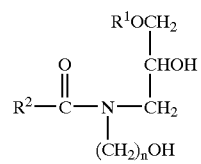

(1)

wherein $R^1$ represents a hydrocarbon group having 10 to 26 carbon atoms, $R^2$ represents a hydrocarbon group having 9 to 25 carbon atoms, and n stands for an integer of from 2 to 6.

In the formula, $R^1$ may preferably be a linear or branched alkyl or alkenyl group having 10 to 26 carbon atoms, with an alkyl group having 10 to 18 carbon atoms being particularly preferred. $R^2$, on the other hand, may preferably be a linear or branched alkyl or alkenyl group having 9 to 25 carbon atoms, with an alkyl group having 9 to 21 carbon atoms being particularly preferred.

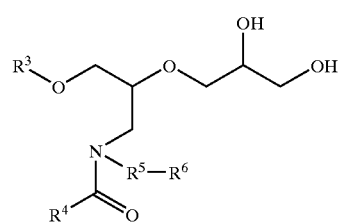

(2)

wherein $R^3$ and $R^4$ are the same or different and each independently represent a hydroxylated or unhydroxylated hydrocarbon group having 1 to 40 carbon atoms, $R^5$ represents an alkylene group having 1 to 6 carbon atoms or a single bond, and $R^6$ represents a hydrogen atom, an alkoxy group having 1 to 12 carbon atoms or a 2,3-dihydroxypropyloxy group with a proviso that $R^6$ is a hydrogen atom when $R^5$ is a single bond.

In the formula, $R^3$ may preferably be a linear or branched alkyl or alkenyl group having 8 to 26 carbon atoms, with an alkyl group having 12 to 22 carbon atoms being particularly preferred. $R^4$ may preferably be a linear or branched alkyl or alkenyl group having 9 to 25 carbon atoms, with an alkyl group having 11 to 21 carbon atoms being particularly preferred. $R^5$ may preferably be a linear or branched alkylene group having 1 to 6 carbon atoms, with a linear or branched alkylene group having 1 to 3 carbon atoms being particularly preferred. $R^6$ may preferably be a hydrogen atom, a linear or branched alkoxy group having 1 to 8 carbon atoms, or a 2,3-dihydroxypropyloxy group.

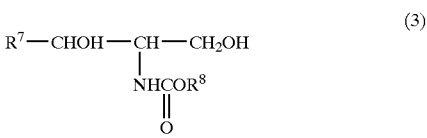

(3)

wherein $R^7$ represents an alkyl or alkenyl group having 11 to 21 carbon atoms, and $R^8$ represents a hydrocarbon group having 3 to 30 carbon atoms.

In the formula, $R^7$ may preferably be an alkyl group having 13 to 17 carbon atoms, and $R_7$ may preferably be a linear or branched alkyl or alkenyl group having 8 to 24 carbon atoms.

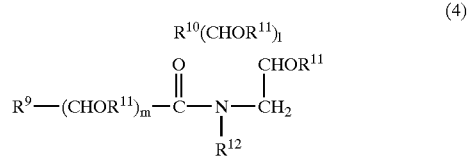

(4)

wherein $R^9$ represents a hydroxylated or unhydroxylated, phosphorylated or unphosphorylated, or sulfated or unsulfated aliphatic hydrocarbon group having 1 to 49 carbon atoms, or a fatty acid residual group having 14 to 22 carbon atoms and represented by a substituent group —$(C_aH_b)$—O—Y in which Y represents a hydrogen atom or an aliphatic hydrocarbon group represented by the following formula:

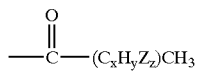

wherein Z represents —OH, —$OP_1$, —$OSO_3^-$ or an epoxy oxygen, x stands for an integer of from 12 to 20, y stands for an integer of 20 to 40, and z stands for an integer of from 0 to 4, a stands for an integer of from 7 to 49, and b stands for an integer of from 10 to 98; $R^{10}$ represents a hydroxylated or unhydroxylated, phosphorylated or unphosphorylated, or sulfated or unsulfated aliphatic hydrocarbon group having 1 to 28 carbon atoms; $R^{11}$ represents a hydrogen atom, a carbohydrate group, a sulfate group or a phosphate group $P_1$ in which $P^1$ represents the following group:

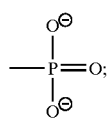

$R^{12}$ represents a hydrogen atom or the following substituent group:

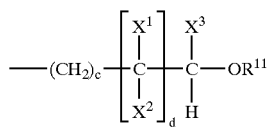

wherein $X^1$, $X^2$ and $X^3$ each independently represent a hydrogen atom or a hydroxylated or unhydroxylated alkyl group having 1 to 5 carbon atoms, c stands for an integer of from 0 to 4, d stands for an integer of 0 or 1, and $R^{11}$ has the same meaning as defined above; and l and m each independently stand for 0 or 1 with the proviso that l+m is 1 or 2 when $R^9$ has 9 to 49 carbon atoms.

In the formula, $R^9$ may preferably be a linear or branched alkyl or alkenyl group having 6 to 32 carbon atoms, with an alkyl group having 10 to 20 carbon atoms being particularly preferred. $R_{10}$ may preferably be a linear or branched alkyl or alkenyl group having 8 to 22 carbon atoms, with an alkyl group having 10 to 20 carbon atoms being particularly preferred.

$R^{11}$ may preferably be a hydrogen atom, and $R^{12}$ may preferably be a hydroxyethyl group.

Among these, ceramide analogues represented by the formula (1) or (2) are particularly preferred.

Examples of the phospholipids can include those disclosed in JP 3-66604 A, which are presented below by formula (5). This publication is also incorporated herein by reference.

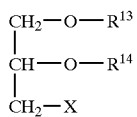

(5)

wherein one of $R^{13}$ and $R^{14}$ represents

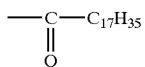

or

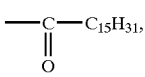

and the other represents a hydrogen atom; and X represents:

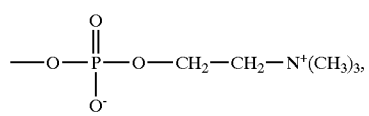

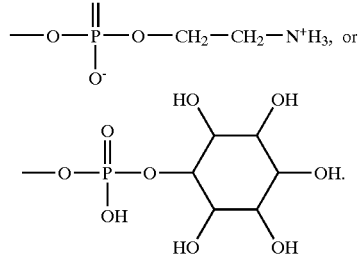

Further, preferred examples of the fatty acid esters of the steroids can include cholesteryl fatty acid esters represented by the following formula (6):

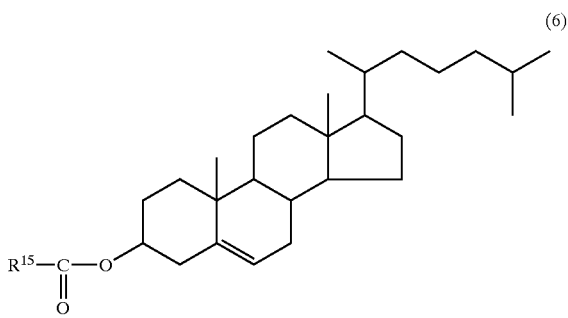

(6)

wherein $R^{15}$ represents a hydroxylated or unhydroxylated hydrocarbon group having 1 to 25 carbon atoms.

The epidermal lipids and their analogues can be used either singly or in combination. They can be added in a proportion of from 0.001 to 60 wt. %, especially from 0.01 to 20 wt. % based on all the ingredients. It is preferred to set the one dose of the bath medicine composition such that their concentration becomes 0.01 ppm or higher, especially ranges from 0.1 to 1,000 ppm in bath water, because this concentration gives excellent feeling of use.

The bath medicine composition according to the present invention can also be added with another oil ingredient and a surfactant. These oil ingredient and surfactant make it possible to provide a self-emulsifying bath medicine composition which makes bath water cloudy and gives good feeling of use.

As the oil ingredient, it is preferred to use one or more compounds selected from glycerides, oils and fats, waxes, hydrocarbons, higher fatty acids, higher alcohols, esters and silicone oils. As the glycerides, diglycerides are preferred, with diglycerides such as the diglyceryl esters of one or more fatty acids, for example, 2-ethylhexanoic acid, myristyl acid, oleic acid and isostearic acid being particularly preferred. Illustrative of the oils and fats are natural oils and fats, such as soybean oil, rice bran oil, jojoba oil, avocado oil, almond oil, olive oil, cacao butter, sesame oil, persic oil, castor ol, coconut oil, mink oil, beef tallow and lard; hardened oils obtained by hydrogenating these natural oils and fats; and synthetic triglycerides such as glycerol myristate and glycerol tri-2-ethylhexanoate. Illustrative of the waxes are carnauba wax, whale wax and beeswax. Illustrative of the hydrocarbons are liquid paraffin, vaseline, paraffin microcrystalline wax, seresine, squalane, and pristane. Illustrative of the higher fatty acids are lauric acid, myristic acid, palmitic acid, stearic acid, behenic acid, oleic acid, linoleic acid, linolenic acid, lanolin acid, and isostearic acid. Illustrative of the higher alcohols are lauryl alcohol, cetyl alcohol, stearyl alcohol, oleyl alcohol, lanolin alcohol, and 2-hexyldecanol. Illustrative of the esters are myristyl lactate, cetyl lactate, isopropyl myristate, myristyl myristate, isopropyl palmitate, isopropyl adipate, butyl stearate, and decyl oleate. Illustrative of the silicone oils are dimethylpolysiloxane, and various silicones.

These oil ingredients can be used either singly or in combination. It is preferred to add them in a proportion of from 0.01 to 99 wt. %, especially from 50 to 95 wt. % based on the whole composition.

As the surfactant, on the other hand, nonionic, cationic, anionic and amphoteric surfactants are all available no matter whether they are natural surfactants or synthetic surfactants. Illustrative nonionic surfactants can include polyoxyethylene alkyl ethers, polyoxyethylene alkylphenyl ethers, polyoxyethylene fatty acid esters, polyoxyethylene sorbitan fatty acid esters, sorbitan fatty acid esters, fatty acid monoglycerides, sugar fatty acid esters, and higher fatty acid alkanols. Typical cationic surfactants can be quaternary ammonium salts. Quaternary ammonium salts can all be used preferably insofar as they are generally available for the body, and those containing the branched quaternary ammonium salts disclosed in JP 61-267505 A are preferred. Illustrative anionic surfactants can include alkyl- or alkenylsulfate salts, alkyl- or alkenylsufate salts added with ethylene oxide and/or propylene oxide, olefinsulfonate salts, alkanesulfonate salts, saturated or unsaturated fatty acid salts, alkyl- or alkenylether carboxylate salts added with ethylene oxide and/or propylene oxide, α-sulfofatty acid salt esters, surfactants of the amino acid type, surfactants of the phosphate ester type, surfactants of the sulfosuccinic acid type, surfactants of the taurin type, and surfactants of the amide ether sulfate type. Illustrative amphoteric surfactants can include amphoteric surfactants of the sulfonic acid type and amphoteric surfactants of the betaine type.

These surfactants can be used either singly or in combination. It is preferred to add them in a proportion of from 0.01 to 90 wt. %, especially from 5 to 20 wt. % based on the whole composition.

To the bath medicine composition according to the present invention, ingredients employed in general bath medicine compositions, for example, inorganic salts, organic acids, vegetable and animal drugs, other essential oils, other perfumes, colors, vitamins, polyhydric alcohols, fine powders, sulfur, deposits of hot-spring water, antiseptics and the like can be added as needed to extents not impairing the effects of the present invention.

To the bath medicine composition according to the present invention, water can be added in an appropriate proportion within a range of from 0.01 to 90 wt. % to increase the stability of the composition or to form the composition into an emulsified form.

The bath medicine composition according to the present invention can be formulated into a desired preparation form such as powder, granules, tablets, capsules, a liquid, or an emulsion by a method known per se in the art. Further, the one dose of the bath medicine composition according to the present invention can be varied as desired, and may range preferably from 1 to 500 g, especially from 5 to 100 g for general home bathtubs of from 150 to 200 liters

EXAMPLES

Example 1
Measurement of IL-4 Production Inhibiting Ability

A 4 mg/mL solution of KLH (Keyhole Limpet Hemocyanin; product of Pierce Chemical Company) and Freund complete adjuvant FCA (Bacto Adjuvant Complete Freund; product of DIFCO) were mixed and emulsified at a volume ratio of 1:1. The resulting emulsion was subcutaneously injected at 200 μL/head to the foreleg paws and hind leg paws of Balb/c mice (female, 8 to 12 weeks old), whereby the mice were sensitized. About 7 days later, axillary and popliteal lymph nodes were excised. After the lymph nodes were washed in PBS, they were loosened between two slide glasses in RPMI medium which had been prepared by adding kanamycin and β-mercapto-ethanol to "RPMI 1640 Medium" (product of BRL) such that their final concentrations became 100 μg/mL and 100 μM, respectively, whereby a suspension of lymphocytes was prepared. The lymphocyte suspension was centrifuged twice at 1,000 rpm for 5 minutes, followed by suspension in the RPMI medium added with 10% FCS. The lymphocytes were spread at $4 \times 10^5$ lymphocytes/well over 96-well plates. Individual compounds or essential oils, which had been prepared at varied concentrations with 10% FCS-added RMPI medium, were added within a final concentration range of from 0.01 to 100 μg/mL. Subsequent to incubation at 37° C. for about 30 minutes in the presence of 5% $CO_2$, KLH was added to give a final concentration of 10 μg/mL. After incubation at 37° C. for 3 days in the presence of 5% $CO_2$, IL-4 in each supernatant was quantitated by ELISA.

For the ELISA quantitation, "Mice IL-4 ELISA Kit" (product of Amersham Corp.) was used. Following a protocol attached to the kit, the quantitation was conducted using recombinant IL-4 as a standard substance. IL-4 production inhibition rates of the individual compounds at the varied concentrations were calculated [100-(IL-4 yield when the sample was added/IL-4 yield in a control added only with the culture medium)×100]. From the IL-4 production inhibition rates, $IC_{50}$ values (concentrations at which IL-4 yields were inhibited by 50%) were determined. The results are presented in Table 1.

As a result, the compounds and essential oils have all been found to inhibit the production of IL-4 at significantly low concentrations compared with the comparative compound (suplatast tosilate). These compounds and essential oils are useful as preventives and improvers or antiallergic agents for atopic dermatitis induced by the production of IL-4.

TABLE 1

| Compound | $IC_{50}$ (μg/mL) |
|---|---|
| Hinokitiol | 0.10 |
| Globulol | 1.08 |
| Epiglobulol | 1.14 |
| Farnesol | 0.59 |
| Guaiol | 0.68 |
| Patchouli alcohol | 0.72 |
| Cedryl acetate | 0.78 |
| Acetylcedrene | 1.60 |
| Santalol | 2.40 |
| Cedrol | 3 |
| Cedrenol | 3.34 |
| Thujopsenol | 3.60 |
| Widdrol | 4.00 |
| Eugenol | 5.60 |
| Menthol | 19.62 |
| Citronellol | 37.28 |
| Cedarwood oil | 0.1 |
| Patchouli oil | 0.2 |
| Pimentoberry resinoid | 0.2 |
| Vetiver oil | 1.0 |
| Sandalwood oil | 2.4 |
| Bay oil | 3.7 |
| Eucalyptus oil | 4.0 |
| Clove oil | 8.2 |
| Chamomile oil | 13.5 |
| Guaiacwood oil | 20.2 |
| Ginger oil | 28.8 |
| Cumin oil | 39.9 |
| Suplatast tosilate | 50 |

Example 2
Effects on Allergy to House Dust Mite Antigen

Tape stripping was done 8 times with an adhesive cellophane tape (product of Nichiban Co., Ltd.) to shaved abdominal parts of Balb/c mice (female). The abdominal parts were coated with 50-μL portions of a house dust mite antigen, which had been obtained by dialyzing an allergen scratch extract "DANI" (product of Torii Pharmaceutical Co., Ltd.) and then concentrating the dialyzate ten-fold by ultrafiltration, so that the mice were sensitized. One, four, five and six days later, 20 μL portions of cedrol, cumin oil and cedarwood oil of concentrations shown in Table 2 (prepared by dissolving them in 70% ethanol solution) were topically applied onto one ears, respectively, and the same amount of the solvent control (70% ethanol solution) was applied at the others. Seven days after the sensitization, the mice were challenged on the dorsal ear lobe by subcutaneous injection of 10 μL of the same angiten solution. To measure ear swelling caused by nonspecific stimulation with the house dust mite antigen, 10-μL portions of the house dust mite antigen were subcutaneously injected to one ear lobes of unsensitized mice. Three and twenty hours after the stimulation, the ear lobes of the anesthetized mice were covered with pieces of paper towel soaked with purified water of 40° C., respectively. After that, 20 μL portions of the individual compounds were topically applied to one ears, respectively, while to the other, the same amount of the solvent control were applied. Twenty-four hours after stimulation, the thicknesses of the ears were measured by a thickness gauge, and differences from the thicknesses of the corresponding ears before the stimulation were recorded as ear swellings. Each ear swelling inhibition rate (%) was determined by the following formula: [ear swelling (solvent control)−ear swelling (sample)]/[ear swelling (solvent control)−ear swelling (nonspecific stimulation by the house dust mite antigen)]×100. Differences in swelling between the ear applied with the solvent control and the corresponding ears applied with the samples, respectively, were statistically analyzed by t-test, and any difference with significance level lower than 5% was considered statistically significant. The results are presented in Table 2.

As a result, each compound showed the inhibitory effects for allergy to the house dust mite antigen at all the concentrations. Among the compounds, cedrol and globulol showed marked effects at the concentrations of 0.1% and 1.0% (statistically significant at 1% or 5 % significance level).

TABLE 2

| Invention Compound Concentration | Cedrol | | | Globulol | | | Cumin oil | | Cedarwood oil | |
|---|---|---|---|---|---|---|---|---|---|---|
| (W/V %) | 0.01 | 0.10 | 1.00 | 0.01 | 0.10 | 1.00 | 0.10 | 1.00 | 0.10 | 1.00 |
| Swelling inhibition rate (%) | 8 | 14 | 13 | 11 | 19 | 26 | 8 | 7 | 8 | 7 |
| S.E. | 6.5 | 3.4 | 2.1 | 9.2 | 14.0 | 11.7 | 4.4 | 8.2 | 8.8 | 5.8 |

Example 3

Cedrol (0.1 g), cholesterol (0.5 g), cholesteryl isostearate (1 g), polyether-modified silicone (1.5 g), cyclic silicone (20 g), methylphenylpolysiloxane (2 g), methylpolysiloxane (2 g), magnesium sulfate (0.5 g), 55% ethanol (5 g), carboxymethylchitin (0.5 g), ceramide (0.5 g) and purified water were mixed into a cream (100 g). The cream so obtained had excellent IL-4 production inhibiting ability, antiallergic ability, and atopic dermatitis preventing and improving ability.

Example 4

Patchouli alcohol (0.15 g), cholesterol (1.5 g), polyether-modified silicone (1.5 g), cyclic silicone (20 g), methylpolysiloxane (4 g), magnesium sulfate (0.5 g), 55% ethanol (5 g), carboxymethylchitin (0.5 g), ceramide (0.5 g) and purified water were mixed into a cream (100 g). The cream so obtained had excellent IL-4 production inhibiting ability, antiallergic ability, and atopic dermatitis preventing and improving ability.

Example 5

A cream (100 g) was formulated in a similar manner as in Example 4 except that the patchouli alcohol was replaced by menthol (0.2 g). The cream so obtained had excellent IL-4 production inhibiting ability, antiallergic ability, and atopic dermatitis preventing and improving ability.

Example 6

Cedrol (0.1 g), crystalline cellulose (55 g) and a 10% solution of hydroxypropylcellulose in ethanol (35 g) were mixed and kneaded into a homogeneous mass. Subsequent to granulation by an extrusion granulator, the resulting green granules were dried and then sifted into a granular preparation. The granular preparation so obtained had excellent IL-4 production inhibiting ability, antiallergic ability, and atopic dermatitis preventing and improving ability.

Example 7

Patchouli oil (0.1 g), cholesterol (0.5 g), cholesteryl isostearate (1 g), polyether-modified silicone (1.5 g), cyclic silicone (20 g), methylphenylpolysiloxane (2 g), methylpolysiloxane (2 g), magnesium sulfate (0.5 g), 55% ethanol (5 g), carboxymethylchitin (0.5 g), ceramide (0.5 g) and purified water were mixed into a cream (100 g). The cream so obtained had excellent IL-4 production inhibiting ability, antiallergic ability, and atopic dermatitis preventing and improving ability.

Example 8

Cedarwood oil (1.0 g), cholesterol (1.5 g), polyether-modified silicone (1.5 g), cyclic silicone (20 g), methylpolysiloxane (4 g), magnesium sulfate (0.5 g), 55% ethanol (5 g), carboxymethylchitin (0.5 g), ceramide (0.5 g) and purified water were mixed into a cream (100 g). The cream so obtained had excellent IL-4 production inhibiting ability, antiallergic ability, and atopic dermatitis preventing and improving ability.

Example 9

A cream (100 g) was formulated in a similar manner as in Example 8 except that the cedarwood oil was replaced by sandalwood oil (0.2 g). The cream so obtained had excellent IL-4 production inhibiting ability, antiallergic ability, and atopic dermatitis preventing and improving ability.

Example 10

Vetiver oil (0.1 g), crystalline cellulose (55 g) and a 10% solution of hydroxypropylcellulose in ethanol (35 g) were mixed and kneaded into a homogeneous mass. Subsequent to granulation by an extrusion granulator, the resulting green granules were dried and then sifted into a granular preparation. The granular preparation so obtained had excellent IL-4 production inhibiting ability, antiallergic ability, and atopic dermatitis preventing and improving ability.

Example 11

Globulol (product of Fluka Chemical Corp., purity: 99%; 0.1 g), cholesterol (0.5 g), cholesteryl isostearate (1 g), polyether-modified silicone (1.5 g), cyclic silicone (20 g), methylphenylpolysiloxane (2 g), methylpolysiloxane (2 g), magnesium sulfate (0.5 g), 55% ethanol (5 g), carboxymethylchitin (0.5 g) and purified water were mixed into a cream (100 g). The cream so obtained had excellent IL-4 production inhibiting ability, antiallergic ability, and atopic dermatitis preventing and improving ability.

Example 12

Epiglobulol (product of Fluka Chemical Corp., purity: 95%; 1.0 g), cholesterol (1.5 g), polyether-modified silicone (1.5 g), cyclic silicone (20 g), methylpolysiloxane (4 g), magnesium sulfate (0.5 g), 55% ethanol (5 g), carboxymethylchitin (0.5 g) and purified water were mixed into a cream (100 g). The cream so obtained had excellent IL-4 production inhibiting ability, antiallergic ability, and atopic dermatitis preventing and improving ability.

Example 13

Globulol (product of Fluka Chemical Corp., purity: 99%; 0.1 g), crystalline cellulose (55 g) and a 10% solution of hydroxypropylcellulose in ethanol (35 g) were mixed and kneaded into a homogeneous mass. Subsequent to granulation by an extrusion granulator, the resulting green granules were dried and then sifted into a granular preparation. The granular preparation so obtained had excellent IL-4 production inhibiting ability, antiallergic ability, and atopic dermatitis preventing and improving ability.

Preparation Example 1

Preparation of Ceramide Formulation

Employed were the following compounds (a), (b) and (c), which had been prepared in accordance with the process described in Referential Example 1 of JP 63-192703 A.

Compound (a): N-(3-hyxadecyloxy-2-hydroxypropyl)-N-2-hydroxyethylhexadecanamide [$R^4=C_{16}H_{33}$, $R^5=C_{15}H_{31}$ in the formula (9)].

Compound (b): N-(3-hexadecyloxy-2-hydroxypropyl)-N-2-hydroxyethyldecanamide [$R^4=C_{16}H_{33}$, $R^5=C_9H_{13}$ in the formula (9)].

Compound (c): N-(2-hycroxy-3-tetradecyloxypropyl)-N-2-hydroxyethyldecanamide [$R^4=C_{14}H_{29}$, $R^5=C_9H_{19}$ in the formula (9)].

A 1:1:1 mixture of the compound (a), compound (b) and compound (c) and cholesteryl hemisuccinate were weighed such that they amounted to 50%, respectively. They were heated to about 80° C., at which the compounds (a), (b) and (c) and the cholesteryl hemisuccinate were completely dissolved. Needless to say, the mixing ratio of the compound (a), compound (b) and compound (c) in the mixture is not limited to the above ratio but can be varied as desired.

Example 14

Liquid medicinal bath preparations of the formulations shown in Table 3 were prepared in a manner known per se in the art, and their skin roughness/dryness improving effects and skin characteristic improving effects were ranked. The results are also presented in Table 3.

(Ranking Method)

(1) Degree of Improvements on Skin Roughness/Dryness

Each medicinal bath preparation was ranked for the degree of improvements on skin roughness and/or dryness as will be described hereinafter. After the medicinal bath preparation was dissolved in a home bathtub (40° C., 150 to 200 L), ten female panellers (20 to 30 years old) suffering from marked skin roughness and/or dryness took a bath for 10 minutes. After they used the medicinal bath preparation once a day for 1 week, the conditions of skin roughness and/or dryness were compared with those of skin roughness and/or dryness before the use, and were ranked in accordance with the following standard. The results were indicated in terms of average scores.

5: Considerably improved over the condition before use.

4: Fairly improved over the condition before use.

3: Slightly improved over the condition before use.

2: Not different substantially from the condition before use.

1: Not different at all from the condition before use.

0: Deteriorated.

(2) Degree of Improvements on Skin Characteristics

Each medicinal bath preparation was ranked for the degree of improvements on skin characteristics as will be described hereinafter. Ten panellers (20 to 30 years old), who were conscious of their sensitive skins, used the medicinal bath preparation once a day for 1 month in a similar manner as in the above-described evaluation. The susceptibility to skin roughness and/or dryness in daily life was compared with that before the use and was ranked in accordance with the following standard. The results were indicated in terms of average scores.

5: Considerably prevented compared with the susceptibility to skin roughness and/or dryness before use.

4: Fairly prevented compared with the susceptibility to skin roughness and/or dryness before use.

3: Slightly prevented compared with the susceptibility to skin roughness and/or dryness before use.

2: Not different substantially from the susceptibility to skin roughness and/or dryness before use, with occasional occurrence of skin roughness and/or dryness.

1: Not different at all from the susceptibility to skin roughness and/or dryness before use, with frequent occurrence of skin roughness and/or dryness.

0: More susceptible to skin roughness and/or dryness than before use.

TABLE 3

|  | Invention product | | | | | Comp. product | |
|---|---|---|---|---|---|---|---|
|  | 1 | 2 | 3 | 4 | 5 | 1 | 2 |
| Cedrol | 0.1 | 1 | 0.5 | — | 1 | — | — |
| Patchouli Alcohol | — | — | 0.5 | — | — | — | — |
| Cedarwood oil[1)] | — | — | — | 1 | — | — | — |
| Ceramide formulation of Prod. Ex. 1 | — | — | — | — | 1 | 1 | — |
| Isopropyl myristate | 20 | 20 | 20 | 20 | 20 | 20 | 20 |
| Liquid paraffin | Bal. | Bal. | Bal. | Bal. | Bal. | Bal. | Bal. |
| Perfume | q.v. | q.v. | q.v. | q.v. | q.v. | q.v. | q.v. |
| Polyoxyethylene oleyl ether (12EO) | 10 | 10 | 10 | 10 | 10 | 10 | 10 |
| Polyoxyethylene oleyl ether (4EO) | 6 | 6 | 6 | 6 | 6 | 6 | 6 |
| Methyl paraoxybenzoate | 0.1 | 0.1 | 0.1 | 0.1 | 0.1 | 0.1 | 0.1 |
| Butyl paraoxybenzoate | 0.1 | 0.1 | 0.1 | 0.1 | 0.1 | 0.1 | 0.1 |
| Total | 100 | 100 | 100 | 100 | 100 | 100 | 100 |
| One dose (150 to 200 L bathwater) | 30 mL | 30 mL | 30 mL | 30 mL | 30 mL | 30 mL | 30 mL |
| Degree of improvements on skin roughness and/or dryness | 3.0 | 3.8 | 4.2 | 4.0 | 5.0 | 2.5 | 0.8 |
| Degree of improvements on skin characteristics | 3.2 | 4.4 | 4.8 | 4.6 | 4.9 | 1.8 | 1.0 |

[1)]Cedrol content: 24%

Example 15

Invention product 5 and Comparative product 1, both of which are shown in Table 3, were used for 1 month by 25 patients (invention product: 13 patients, comparative product: 12 patients) who had been diagnosed suffering from atopic dermatitis and were under treatment by a dermatologist. Their skin conditions determined by an expert skilled in skin diagnosis in comparison with the conditions before the use were ranked by the following standard. In this application test, a double blind test was designed, and the panellers and the skin diagnosis expert were both kept out of information on the ingredients of the used medicinal bath preparations.

<Ranking Standard>

3: Improved.

2: Unchanged.

1: Deteriorated.

The results are presented in Table 4.

TABLE 4

|  | Invention product 5 | Comparative product 1 |
|---|---|---|
| Improved | 11 patients | 5 patients |
| Unchanged | 2 patients | 5 patients |
| Deteriorated | 0 patient | 2 patients |

Invention product 5 was recognized to have improved the skin conditions by about 85% of the panellers, and showed higher improving effects than Comparative product 1. Incidentally, between the group in which Invention product 5 was used (13 patients) and the group in which Comparative product 1 was used (12 patients), no significant difference was observed in connection with age, sex, severity and the drugs used in combination.

Example 16

A powder-type medicinal bath preparation of the following formulation was prepared.

TABLE 5

|  | % |
|---|---|
| Farnesol | 1 |
| Sodium sulfate | 5 |
| Sodium hydrogencarbonate | Balance |
| Sodium carbonate | 30 |
| Calcium silicate | 1 |
| Perfume | q.v. |
| Color | q.v. |
| One dosage (150 to 200 L bathwater) | 30 g |

Example 17

A tablet-type medicinal bath preparation of the following formulation was prepared.

TABLE 6

|  | % |
|---|---|
| Vetiverol | 1 |
| Sodium hydrogencarbonate | 25 |
| Sodium carbonate | Balance |
| Fumaric acid | 45 |
| Calcium silicate | 1 |
| Perfume | q.v. |
| Color | q.v. |
| One dosage (150 to 200 L bathwater) | 50 g |

Capability of Exploitation in Industry

IL-4 production inhibitors which comprise the above-described IL-4 production inhibiting substances show superb IL-4 production inhibitory activity and are excellent in percutaneous or transdermal absorption, stability and safety. Further, antiallergic agents and atopic dermatitis preventives and improvers, which comprise the above-described IL-4 production inhibiting substances, have preventing and improving effects for allergic symptoms such as atopic dermatitis.

The bath medicine compositions according to the present invention, on the other hand, are highly effective for improving skin roughness and dryness and have effect for improving the skin characteristics of overdrying or oversensitive skin.

What is claimed:

1. A method of suppressing interleukin-4 production comprising administering to a subject in need thereof a composition comprising an effective amount of cedrol.

2. The method of claim 1, wherein said composition further comprises at least one compound selected from the group consisting of Hinokitiol, epiglobulol, acetylcedrene, cedarwood oil, patchouli oil, pimentoberry resinoid, vetiver oil, sandalwood oil, globulol, farnesol, guaiol, patchouli alcohol, cedryl acetate, and santalol.

3. The method of claim 2, wherein the compound is Hinokitiol.

4. The method of claim 2, wherein the compound is epiglobulol.

5. The method of claim 2, wherein the compound is acetylcedrene.

6. The method of claim 2, wherein the compound is cedarwood oil.

7. The method of claim 2, wherein the compound is patchouli oil.

8. The method of claim 2, wherein the compound is pimentoberry resinoid.

9. The method of claim 2, wherein the compound is vetiver oil.

10. The method of claim 2, wherein the compound is sandalwood oil.

11. The method of claim 2, wherein the compound is globulol.

12. The method of claim 2, wherein the compound is farnesol.

13. The method of claim 2, wherein the compound is guaiol.

14. The method of claim 2, wherein the compound is patchouli alcohol.

15. The method of claim 2, wherein the compound is cedryl acetate.

16. The method of claim 2, wherein the compound is santalol.

17. The method of claim 1, wherein the composition is administered as an external skin preparation, an oral preparation, an injection, an inhalant, or a medicinal bath.

18. The method of claim 1, wherein the composition further comprises one or more additives selected from the group consisting of an oil, an oil/water emulsified base, an water/oil emulsified base, water, an anti-inflammatory analgesic, a disinfectant, a vitamin, an emollient, a humectant, an ultraviolet absorber, a chelating agent, a pH regulator, an antiseptic, a thickener, an alcohol, a coloring agent, a perfume, an epidermal lipid, a surfactant, an inorganic salt, an organic acid, a polyhydric alcohol, sulfur, and a deposit of hot-spring water.

19. The method according to claim 1, wherein cedrol is administered in an oral form and wherein said effective amount of cedrol is at a daily dose of from 0.001 to 2000 mg per adult.

20. The method according to claim 1, wherein cedrol is administered as a bath medicine composition and wherein said effective amount of cedrol ranges from 0.01 to 20 weight % based on all the ingredients of said bath medicine composition.

21. The method according to claim 20, wherein cedrol is administered as a bath medicine composition and wherein said effective amount of cedrol ranges from 1 to 10 weight % based on all the ingredients of said bath medicine composition.

* * * * *